United States Patent
Kartäusch

(10) Patent No.: US 11,224,355 B2
(45) Date of Patent: Jan. 18, 2022

(54) MR IMAGING WITH OPTIMIZED IMAGING WORKFLOW

(71) Applicant: Ralf Kartäusch, Erlangen (DE)

(72) Inventor: Ralf Kartäusch, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 134 days.

(21) Appl. No.: 15/456,045

(22) Filed: Mar. 10, 2017

(65) Prior Publication Data
US 2017/0258360 A1 Sep. 14, 2017

(30) Foreign Application Priority Data
Mar. 10, 2016 (DE) .......................... 102016203940.7

(51) Int. Cl.
*A61B 5/055* (2006.01)
*G01R 33/54* (2006.01)
(Continued)

(52) U.S. Cl.
CPC ................ *A61B 5/055* (2013.01); *A61B 5/08* (2013.01); *A61B 5/113* (2013.01); *A61B 5/742* (2013.01);
(Continued)

(58) Field of Classification Search
None
See application file for complete search history.

(56) References Cited

U.S. PATENT DOCUMENTS

2003/0188757 A1* 10/2003 Yanof .................. A61B 5/1135
600/427
2005/0113673 A1* 5/2005 Avinash ................ A61B 5/055
600/413
(Continued)

FOREIGN PATENT DOCUMENTS

DE 102013222103 A1 5/2015
WO 2015092062 A1 6/2015

OTHER PUBLICATIONS

Feng et al. ("Golden-Angle Radial Sparse Parallel MRI: Combination of Compressed Sensing, Parallel Imaging, and golden-Angle Radial Sampling for Fast and Flexible Dynamic Volumetric MRI"; Magnetic Resonance in Medicine, 72:707-717 (2014)).*
(Continued)

*Primary Examiner* — Oommen Jacob
*Assistant Examiner* — Shahdeep Mohammed
(74) *Attorney, Agent, or Firm* — Lempia Summerfield Katz LLC

(57) ABSTRACT

An MR imaging method with an imaging workflow is provided. Within the scope of the MR imaging method, at least one breath-holding command is output to a patient. An MR imaging is performed with an MR imaging method that may be used with free breathing. A breathing movement of the patient is detected based on measured data acquired when performing the MR imaging method. A time relationship is determined between the breathing movement of the patient and the breath-holding command. The imaging workflow is modified as a function of the determined time relationship. A breathing monitoring device and a magnetic resonance imaging system are also provided.

15 Claims, 4 Drawing Sheets

(51) Int. Cl.
    *G01R 33/567*   (2006.01)
    *G01R 33/565*   (2006.01)
    *A61B 5/08*   (2006.01)
    *A61B 5/113*   (2006.01)
    *A61B 5/00*   (2006.01)
    *G01R 33/48*   (2006.01)
    *G01R 33/56*   (2006.01)

(52) U.S. Cl.
    CPC ....... *G01R 33/4824* (2013.01); *G01R 33/543* (2013.01); *G01R 33/5673* (2013.01); *G01R 33/5676* (2013.01); *G01R 33/56509* (2013.01); *G01R 33/5601* (2013.01)

(56) References Cited

U.S. PATENT DOCUMENTS

| | | | | |
|---|---|---|---|---|
| 2005/0119560 | A1* | 6/2005 | Mostafavi | A61B 5/1135 600/425 |
| 2009/0148021 | A1 | 6/2009 | Yui | |
| 2011/0181286 | A1* | 7/2011 | Kamada | A61B 5/055 324/309 |
| 2011/0249880 | A1* | 10/2011 | Parikh | A61B 5/06 382/131 |
| 2014/0024924 | A1* | 1/2014 | Goto | A61B 5/0037 600/413 |
| 2015/0119696 | A1 | 4/2015 | de Oliveira | |
| 2016/0313429 | A1* | 10/2016 | Van Den Brink | G01R 33/283 |

OTHER PUBLICATIONS

German Office Action for German Application No. 102016203940.7, dated Oct. 20, 2017, with English Translation.

German Grant Decision for German Application No. 10 2016 203 940.7, Grant decision dated Feb. 8, 2018, with English Translation.

Feng L. et al. Golden-Angle Radial Sparse Parallel MRI: Combination of Compressed Sensing, Parallel Imaging, and Golden-Angle Radial Sampling of Fast and Flexible Dynamic Volumetric MRI; Magentic Resonance Medicine; vol. 72; pp. 707-717. 2014.

German Office Action for German Application No. 102016203940.7, dated Oct. 20, 2017.

* cited by examiner

MR IMAGING WITH OPTIMIZED IMAGING WORKFLOW

This application claims the benefit of DE 10 2016 203 940.7, filed on Mar. 10, 2016, which is hereby incorporated by reference in its entirety.

BACKGROUND

The present embodiments relate to a magnetic resonance (MR) imaging method with an imaging workflow, a breathing monitoring device, and a magnetic resonance imaging system.

With many examinations with the aid of magnetic resonance imaging (e.g., in the chest or abdomen area), motion artifacts occur on account of the breathing movement of the patient. One approach used to reduce these artifacts is realized in most instances by a temporally clocked workflow of the MR imaging process. This is to be provided if, in addition, contrast agents are still used and the temporal course of the contrast agent is to be attuned to the breathing movement. With such a workflow, the MR imaging is performed during a time interval in which the patient is holding his/her breath. For example, as a function of the contrast agent course, the MR imaging process is divided into a plurality of time sections or time intervals, in which MR signals of an area of the patient to be examined are recorded.

A series of image acquisitions that are distributed over the cited recording time intervals is therefore carried out. These recording time intervals are thus synchronized with the breathing movement of the patient in that the recordings coincide with the resting breathing state of the patient. However, for this to happen, the patient is to regularly hold his/her breath. For example, before starting an image recording sequence, acoustic instructions are issued automatically to the patient to hold his/her breath during the course of the breathing-out process or breathing-in process. Immediately thereafter, the actual MR imaging process (e.g., scan process) or a partial sequence thereof is carried out. However, patients do not always follow the given instructions as desired. Instead, the patient may require additional time until the patient is completely at rest. Therefore, the first image acquisitions of a series of image recordings are in most cases compromised by the movement of the patient.

In addition, a contrast agent may also be used with such a temporally clocked workflow. In this case, a distinction is made between the different phases of the accumulation of the contrast agent. In a first phase, there is still no contrast agent in an area to be examined. An MR image recording is also carried out in this first phase in order subsequently to have available a comparison between a contrast agent-supported image recording and an image recording without contrast agent. In a second phase, the contrast agent flows through the veins of the patient. In a third phase, the contrast agent is located in an area to be examined. There is still a fourth phase (e.g., post contrast phase), in which the contrast agent was already flushed out of the area to be examined. Image recordings are conventionally executed in all four phases. In order to synchronize these image recordings with the respective phases, a test bolus may be provided in advance, for example, with which the temporal course of the accumulation of the contrast agent is determined in advance. In the case of a contrast agent-supported imaging, a clocked workflow therefore additionally includes the synchronization of the image recordings with the individual phases of the contrast imaging. The breath-holding commands are temporally attuned to the individual phases of the contrast agent accumulation.

Alternatively, magnetic resonance imaging methods are used with iterative reconstruction techniques, such as "compressed sensing," for example. Higher time resolutions may be achieved as a result. One example of this is the iGRASP technology (iGRASP—iterative goldenangle radial sparse parallel MR imaging—iterative magnetic resonance imaging method with parallel subscanning with a radial k-space trajectory, the adjacent radial trajectory segments of which in the golden angle are oriented in relation to one another), which is to represent the course of a contrast agent when the patient is breathing freely. This technology allows a diagnostically relevant image quality to be achieved in patients who are not able to hold their breath for long enough. The iGRASP technology is shown, for example, in Magnetic Resonance in Medicine; Volume 72, Issue 3, pages 707-717, September 2014. The image quality is, however, frequently reduced in comparison with a standard measurement with breathing commands (e.g., clocked workflow) and cooperative patients. Therefore, in order to achieve an optimal image quality prior to the measurement, an assessment is carried out to determine whether the patient is able to hold air for long enough and whether the clocked workflow may be used. If the patient is not able to do this, the described iGRASP imaging method is employed. Otherwise, the clocked workflow is used. With an incorrect assessment, the quality of the recorded images is possibly not adequate for a diagnosis, or the result of the MR image recording is not optimal.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a magnetic resonance (MR) imaging method for a breathing patient that reliably delivers a good image quality is provided.

In one embodiment, an MR imaging method that may be used when breathing freely is integrated in a workflow in which a breath-holding command is output. A breath-holding command is output to the patient (e.g., automatically). Then, an MR imaging with a motion-insensitive MR imaging method that may be used when breathing freely is started. Such a motion-insensitive MR imaging method that may be used when breathing freely is to be as insensitive to movement as possible. This may be achieved, for example, by an adjusted reconstruction (e.g., compressed sensing), a specific measuring method (e.g., radial scanning), and/or high speed.

During the MR imaging, the patient is thus monitored to determine whether the patient has correctly realized the instruction. The monitoring is carried out by an evaluation of data determined with the MR imaging method that may be used when breathing freely. A breathing movement of the patient is detected based on measurement data acquired when the MR imaging method is performed. The acquired measurement data may be used to determine a time relationship between the breathing movement of the patient and the breath-holding command. This time relationship may then be used for this purpose to modify the imaging workflow as a function of the determined time relationship.

The modification of the workflow may include, for example, adjusting the time instant of outputting the breathing commands to the behavior of the patient. In the case that the patient appears, however, to be uncooperative and completely fails to obey the breathing commands, a minimum quality is provided in the imaging by using an MR imaging method that supplies an adequate imaging quality even when breathing freely. The MR imaging method of one or more of the present embodiments is superior to a method that functions entirely without a breath-holding command, since in terms of cooperation of the patient, the MR imaging method has a better image quality than the former. The method of one or more of the present embodiments is superior to an imaging method that operates with breath-holding commands but is prone to a non-compliance of these commands. An improved imaging quality is achieved by the use of an imaging method that is more robust with respect to a breathing movement and by a monitoring of the breathing movement or of the breath-holding of the patient based on the imaging. As a synergy effect to combining the two approaches, there is the option of monitoring the patient and thus influencing the image quality by additional measures during the imaging.

The breathing monitoring device of one or more of the present embodiments has a command output unit. The command output unit is configured to output a command to the patient to hold his/her breath. The breathing monitoring device of one or more of the present embodiments includes a start command output unit for starting an MR imaging with an MR imaging method that may be used when breathing freely. The breathing monitoring device of one or more of the present embodiments also has a breathing movement detection unit for detecting a breathing movement of the patient based on measurement data acquired when the MR imaging method was performed. The breathing monitoring device of one or more of the present embodiments has a time relationship determination unit for determining a time relationship between the breathing movement of the patient and the breath-holding command. The breathing monitoring device also includes a modification unit for modifying the imaging workflow as a function of the determined time relationship.

The magnetic resonance imaging system of one or more of the present embodiments has a radio-frequency transmit system, a gradient system, and a control device (e.g., a controller). The control device is embodied to actuate the radio-frequency transmit system and the gradient system for a desired measurement based on a predetermined pulse sequence. The magnetic resonance imaging system of one or more of the present embodiments includes a breathing monitoring device of the present embodiments.

Some of the components of the breathing monitoring device may be embodied mainly in the form of software components. This relates, for example, to the command output unit, the breathing movement detection unit, the time relationship determination unit, and the modification unit. These components, however, may also be realized in part (e.g., if particularly fast calculations are to be performed) in the form of software-supported hardware components (e.g., FPGAs or the like). Similarly, if, for example, what is concerned is merely a transfer of data from other software components, the interfaces may also be configured as software interfaces. In one embodiment, however, the interfaces may also be configured as interfaces constructed with hardware that are controlled by suitable software.

A realization largely through software has the advantage that conventionally used control devices of magnetic resonance imaging systems may also be upgraded easily with a software update in order to operate in the manner according to one or more of the present embodiments. In this respect, a suitable computer program product with a computer program that may be loaded directly into a memory storage device (e.g., a non-transitory computer-readable storage medium) of a magnetic resonance imaging system and/or into a memory storage device (e.g., a non-transitory computer-readable storage medium) of a control device of a magnetic resonance imaging system and has program portions (e.g. instructions) in order to carry out all the acts of the method when the computer program is executed in the control device is provided.

Such a computer program product may include, in addition to the computer program, additional components such as, for example, documentation and/or additional components, and hardware components such as, for example, a hardware key (e.g., dongles) for use of the software.

A computer-readable medium (e.g., a non-transitory computer-readable storage medium such as a memory stick, a hard disk or another transportable or firmly installed data carrier on which the program portions of the computer program that may be read in and executed by a computer unit of the control device or of the magnetic resonance imaging system are stored) may serve for transport to the memory storage device of the control device and/or for storage in the magnetic resonance imaging system. For this purpose, the computer unit may, for example, have one or more cooperating microprocessors or the like.

The claims of one claim category may also be further developed similarly to the claims of another claim category. In addition, within the context of the present embodiments, the various features of different exemplary embodiments and claims may also be combined to form new exemplary embodiments.

In one embodiment of the MR imaging method, upon determination of the time relationship, it is determined whether the patient has actually realized the breath-holding command. Within the scope of the modification act, a decision will be made as to whether the breath-holding command is to be completely omitted. This may be useful, for example, if the patient reacts to breathing commands in a completely unpredictable manner or too slowly. If the output of the breath-holding command is completely omitted, the MR imaging is carried out in accordance with one or more of the present embodiments with a robust MR imaging method in relation to a breathing movement or a robust MR pulse sequence in relation to a breathing movement, so that a good image quality is achieved during the examination despite the inadequate cooperation of the patient.

The determination of the time relationship may include the determination with which time delay the breath-holding command was executed by the patient. A time difference between the time instant of outputting the breath-holding command and the occurrence of the resting breathing state is determined, for example. Within the context of the modification act, a decision is made to determine whether and how the time instant of the breath-holding command is to be changed and/or whether and how the start time of the MR imaging is to be modified. Therefore, a temporal adjustment both of the time instant of outputting the breathing command and also the time instant of the start of the imaging or an imaging sequence, which are selected such that the time interval of the resting breathing state and the time interval of an imaging coincide, may be carried out. This now permits the acquisition of MR signals to be carried out during the resting state of the patient, so that the image quality of the MR image recording is improved.

A test run may be performed for the determination of the time difference between the time instant of outputting the breath-holding command and the occurrence of the resting breathing state, and the subsequent MR imaging or the associated imaging workflow is performed by taking the determined time difference into account. With this variant, the workflow is therefore carried out already at the start of the image recording with adjusted time parameters, so that the image quality of the first acquisitions is also expected to be very good. In addition, the breathing movement of the patient is also monitored during the MR image recording, so that the respective start time instant of the recording time intervals may be adjusted to a possible change in behavior of the patient.

In one embodiment of the MR imaging method, the imaging method is contrast agent-supported. With a contrast agent-supported MR imaging method, a contrast agent is injected into the patient in advance (e.g., before the examination). The contrast agent moves with the circulation of the patient to an area to be examined. Once the contrast agent arrives there, the contrast agent may be used for an MR image recording with improved image contrast. In order to achieve a synchronization of the arrival of the contrast agent in the area to be examined with the time instant of an MR image recording, a test bolus may be used in advance. Such a test bolus only has a minimal quantity of the contrast agent that is used subsequently for the MR imaging. After injecting the test bolus, the time instant of arrival of the test bolus in the area to be examined is determined. In this way, the temporal behavior or duration that an injected contrast agent requires in order to reach an area to be examined, is known. The MR imaging workflow is then performed by additionally taking into account the determined time instant of the arrival of the test bolus. The test bolus may be acquired in a test run before the actual imaging process. In this way, the arrival of the contrast agent bolus may be attuned to the imaging workflow, so that an improved image contrast is achieved.

In one variant of the contrast-supported MR imaging method, the time instant of outputting the instruction to hold his/her breath is selected such that the expected time instant of the patient holding his/her breath coincides with the time instant of the arrival of a contrast agent bolus in the area to be examined (e.g., in the area in which a contrast agent-supported imaging is performed). In this way, the imaging is carried out under optimal contrast conditions and, at the same time, during the resting breathing state of the patient, so that an optimal image quality may be achieved with an optimal contrast.

In one variant of the MR imaging method, an imaging method with iterative reconstruction technology is used as an MR imaging method. Despite subscanning of a signal, high quality images may be generated, thereby achieving a high time resolution, for example, with the aid of an iterative reconstruction.

An imaging method with radial scanning may be used as an MR imaging method. A radial MR imaging method is advantageous in that the radial MR imaging method is robust with regards to movements. The imaging method may be an iGRASP imaging method, for example.

The measurement data determined with the MR imaging method in the detection act of a breathing movement of the patient may include raw data, for example. For example, the raw data may have data from magnetic resonance signals from the k-space center of a trajectory used in the imaging for scanning the k-space. No image data has to be reconstructed for a detection of the breathing movement of the patient (e.g., the acquired raw data need not be transformed into the image data space). A reconstruction with the aid of a transformation of the raw data into the image data space is computationally complicated and uses considerable computing capacity and time. Since the reconstruction of image data may be dispensed with in the MR imaging method for the detection of the breathing behavior of the patient, the detection of the breathing movement may be performed rapidly (e.g., in real-time).

The MR imaging method may have a clocked workflow as an imaging workflow. A clocked workflow is well suited to an interactive imaging, in which information about the movement of the patient is collected and the breathing movement of the patient is influenced such that the breathing movement of the patient remains in the resting breathing state during the time interval of an MR imaging.

DETAILED DESCRIPTION

Figure 1:
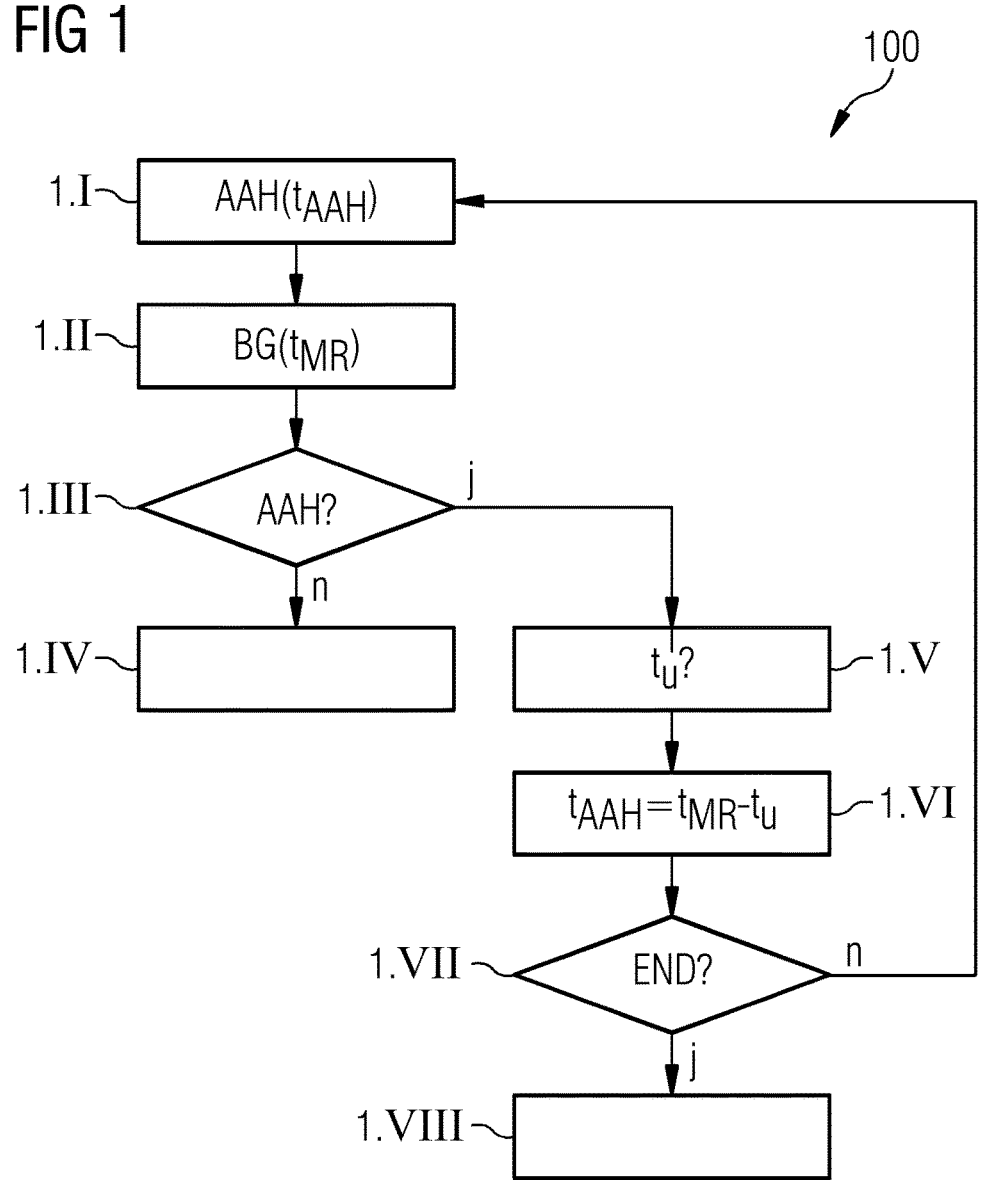
FIG. 1 shows a flow diagram that illustrates a contrast-enhanced MR imaging method according to an exemplary embodiment.

FIG. 1 shows a flow diagram 100 that illustrates a contrast-enhanced magnetic resonance (MR) imaging method according to an exemplary embodiment. In act 1.I, an acoustic command AAH($t_{AAH}$) to the patient to hold his/her breathing movement is issued firstly automatically at a time instant $t_{AAH}$. In this exemplary embodiment, this occurs within the scope of a clocked workflow. In act 1.II, a contrast-enhanced MR imaging BG($t_{MR}$) that also delivers an acceptable image quality with free breathing is then started at a time instant $t_{MR}$. A contrast agent was provided in advance for the contrast-enhanced imaging. An iGRASP method may be used as an imaging method, for example. In act 1.III, it is determined whether the breath-holding command AAH is actually realized. This may take place based on measurement data acquired with the aid of the iGRASP method. For example, the raw data of the k-space center acquired with the MR image recording is used as a breathing signal (e.g., as proof as to whether or not a breathing movement has taken place). In the case that there has been absolutely no holding of breath, which is indicated in FIG. 1 with "n", a move is made to act 1.IV. In act 1.IV, the MR imaging is then continued entirely without the breath-holding command AAH and finally terminated. Since an iGRASP method that is particularly robust with regard to a breathing movement of a patient is used for the MR imaging, despite omitting the breath-holding commands conventional for the clocked workflow, an acceptable image quality is achieved.

If it was detected that breath was being held, which is identified in FIG. 1 with "y", a move is made to act 1.I, in which the time instant $t_u$ at which the breath-holding command AAH was realized by the patient is determined. Then in act 1.VI, a time instant $t_{AAH}$ of a breath-holding command AAH is adjusted to the reaction time $t_u$ of the patient, whereby the following applies $$t_{AAH}=t_{MR}-t_u. \tag{1}$$

A check is carried out in act 1.VII to determine whether the imaging is to be terminated, for example, because sufficient measurement data was already acquired. If this is the case, which is indicated in FIG. 1 with "y", the imaging is terminated in act 1.VIII. If the imaging has still not come to an end, which is indicated in FIG. 1 with "n", a move back to act 1.I is made, and a breath-holding command is output at the new time instant $t_{AAH}(t_u)$, etc.

Figure 2:
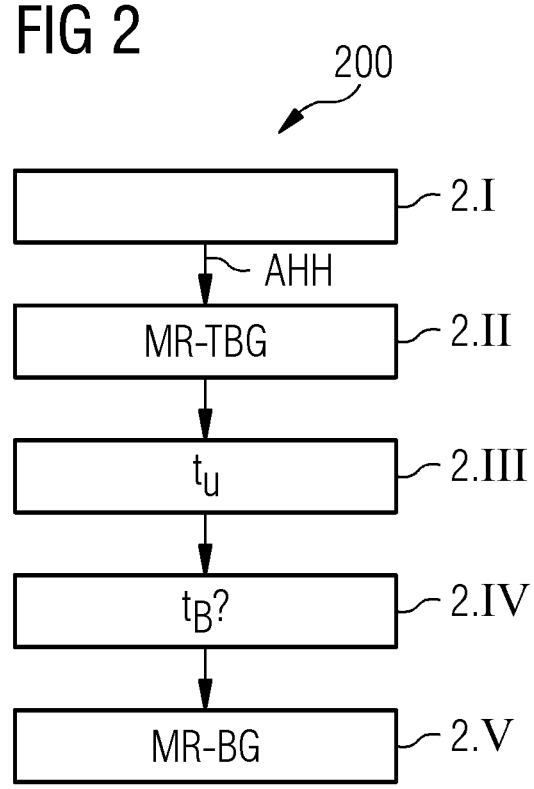
FIG. 2 shows a flow diagram that illustrates a contrast-enhanced MR imaging method according to a second exemplary embodiment.

A flow diagram 200 is shown in FIG. 2, which illustrates a contrast-enhanced MR imaging method according to a second exemplary embodiment. In this variant, a type of upstream test run is used to determine both the reaction time $t_u$ of the patient and also the bolus time $t_B$ during which a contrast agent bolus arrives at an area to be examined. The time instant of starting the imaging $t_{MR}$ and the time instant $t_{AAH}$ of outputting the breath-holding command may thus be attuned to the determined times $t_u$, $t_B$. Before starting the method, a test bolus is given to the patient. In other words, a small quantity of contrast agent is injected into the patient in advance. In act 2.I, a breath-holding command AAH is given to the patient. Then an MR test imaging MR-TBG is started in act 2.II at a test start time instant $t_{MR}$. A reaction time $t_u$ of the patient to the breath-holding command AAH is determined in act 2.III based on the recorded test images. A time $t_B$ is determined in act 2.IV based on the measurement data recorded in the test imaging MR-TBG, at which the test bolus has arrived at an area to be examined. In act 2.V, the actual contrast-enhanced imaging MR-BG takes place with a breath-holding command, which is attuned to the determined times $t_B$, $t_u$. For example, the time instant of starting the imaging $t_{MR}$ and the time instant $t_{AAH}$ of outputting the breath-holding command are thus attuned to the determined times $t_u$, $t_B$. The subsequent MR image recording is then started at time instant $t_{MR}$ if the contrast agent bolus has arrived at an area to be examined. The following thus applies:

$$t_{MR}=t_B. \tag{2}$$

Together with the equation 1, the following results for the time instant $t_{AAH}$ of the breath-holding command:

$$t_{AAH}=t_B-t_u. \tag{3}$$

In this way, the arrival of the contrast agent bolus in the area to be examined and the image recording and the resting breathing state of the patient are synchronized so that a good image quality is to be expected with an increased contrast.

Figure 3:
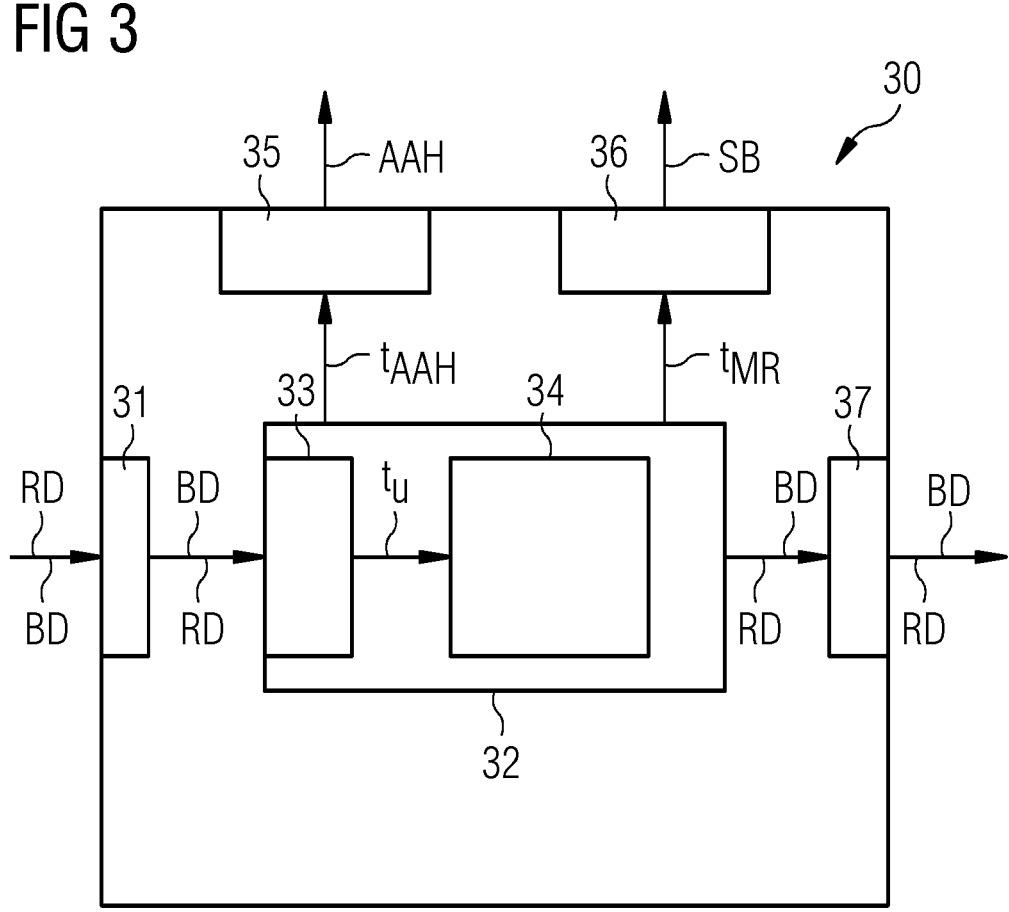
FIG. 3 shows a block diagram that illustrates a breathing monitoring device according to an exemplary embodiment.

A breathing monitoring device 30 according to an exemplary embodiment is shown schematically in FIG. 3. The breathing monitoring device 30 may be, for example, part of a control device of a magnetic resonance imaging system (see FIG. 4). The breathing monitoring device 30 includes a data acquisition unit 31 that receives raw data RD or also image data BD of an area to be examined, for example, acquired or reconstructed within the scope of an MR imaging method. The data RD, BD is transferred to a breathing movement detection unit 32. The breathing movement detection unit 32 evaluates the acquired data RD, BD in order to determine whether and at which time instant a breath-holding command was performed by a patient. For example, a k-space center signal (e.g., raw data) acquired from the k-space center with the aid of the magnetic resonance imaging method may be evaluated herefor.

The breathing movement detection unit 32 includes a time relationship determination unit 33 for determining a time relationship between the breathing movement of the patient and the breath-holding command AAH. For this purpose, the time relationship determination unit 33 determines a time instant at the start of a resting breathing state based on the acquired raw data RD or image data BD. The time relationship determination unit 33 determines a time difference to between the time instant $t_{AAH}$ of outputting the breath-holding command AAH and the reaction of the patient. The breathing movement detection unit 32 includes a modification unit 34 for modifying the imaging workflow as a function of the determined time relationship. In other words, the modification unit 34 determines correction parameters based on the time difference $t_u$. Correction parameters may have, for example, a modified start time $t_{MR}$ of an MR imaging or a modified time instant $t_{AAH}$ of outputting a breath-holding command AAH.

After evaluating the acquired data RD, BD, the breathing movement detection unit 32 outputs information relating to a modified time instant $t_{AAH}$ of outputting a breath-holding command AAH to a command output unit 35 or alternatively also a command in order to set the output of breath-holding commands AAH entirely. The breathing movement detection unit 32 is also connected to a start command output unit 36. The start command output unit 36 outputs a command SB to start an MR imaging with an MR imaging method that may be used with free breathing. The time instant $t_{MR}$ for outputting the start command SB is, as already explained, likewise determined by the breathing movement detection unit 32 and transferred to the start command output unit 36.

As already mentioned, the time instant $t_{MR}$ for outputting the start command SB and thus the start time instant $t_{MR}$ of the imaging may be associated with the time instant $t_B$ of the arrival of a contrast agent bolus. For example, the time instant $t_B$ of the arrival of the contrast agent may be determined by an MR test imaging MR-TBG performed in advance (e.g., prior to the actual contrast agent imaging). The breathing monitoring device 30 also includes an output interface 37 for outputting received image data BD or received raw data RD, which includes breathing movement data that is forwarded to a display unit (not shown), for example, for graphical representation or to another processing unit for further processing.

Figure 4:
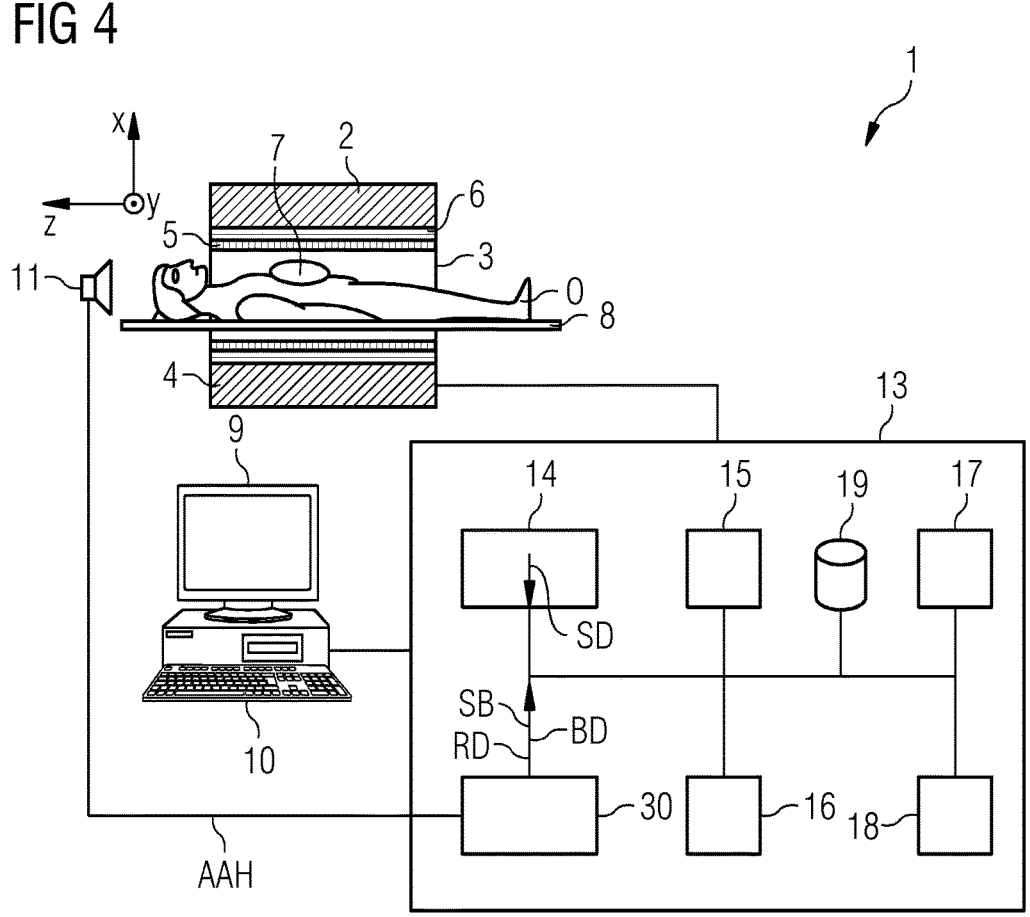
FIG. 4 shows a magnetic resonance imaging system according to an exemplary embodiment.

One embodiment of a magnetic resonance system 1 is shown roughly schematically in FIG. 4 (abbreviated below to "MR system"). The magnetic resonance system 1 includes the actual magnetic resonance scanner 2 with an examination space 3 or patient tunnel, into which an examination object O or a patient or test subject may be introduced on a couch 8. The examination object or the examination area (e.g., a specific organ) may be located in the patient or the test subject.

The magnetic resonance scanner 2 is equipped in the usual manner with a main field magnet system 4, a gradient system 6, and an RF transmitting antenna system 5 and an RF receiving antenna system 7. In the exemplary embodiment shown, the RF transmitting antenna system 5 is a whole body coil fixedly incorporated in the magnetic resonance scanner 2, whereas the RF receiving antenna system 7 consists of local coils to be arranged on the patient or test subject (in FIG. 4 symbolized only by a single local coil). The whole-body coil may be used as an RF receiving antenna system, and the local coils may be used as an RF transmitting antenna system. These coils may each be switched to different operating modes.

The MR system 1 also has a central control device 13 that is used for controlling the MR system 1. This central control device 13 includes a sequence control unit 14 for pulse sequence control. With this, the sequence of radio-frequency pulses (RF pulses) and gradient pulses may be controlled depending on a selected imaging sequence. Such an imaging sequence may be predefined, for example, within a measurement or control protocol. Normally, different control protocols are stored in a memory 19 for different measurements and may be selected by an operator (and where appropriate, altered if need be) and then used to perform the measurement.

For the output of the individual RF pulses, the central control device 13 has a radio-frequency transmitting device 15 that generates the RF pulses, amplifies the RF pulses, and feeds the RF pulses by a suitable interface (not shown in detail) to the RF transmitting antenna system 5. In order to control the gradient coils of the gradient system 6, the control device 13 has a gradient system interface 16. The sequence control unit 14 communicates in a suitable manner, for example, by transmission of sequence control data SD, with the radio-frequency transmitting device 15 and the gradient system interface 16 for transmission of the pulse sequence. The control device 13 also has a radio-frequency receiving device 17 (also communicating in a suitable manner with the sequence control unit 14) in order to acquire magnetic resonance signals (e.g., raw data) in a coordinated manner from the RF transmitting antenna system 7. A reconstruction unit 18 takes over the acquired raw data and reconstructs the MR image data therefrom. This image data may then be stored in a memory 19, for example. The acquired raw data RD or the reconstructed image data BD is further processed in a breathing monitoring device 30 to control and monitor an MR imaging. The breathing monitoring device 30 provides a control command SB to the sequence control unit 14, for example, to start an MR image recording sequence with the aid of the output of sequence control data SD. The breathing monitoring device 30 also includes a connection to an audio communication unit 11 on the magnetic resonance scanner 2 to transmit breath-holding instructions AAH to the patient O.

The central control device 13 may be operated via a terminal with an input unit 10 and a display unit 9, by which the whole MR system 1 may thus also be operated by an operating person. MR images may also be displayed on the display unit 9, and using the input unit 10, if appropriate in combination with the display unit 9, measurements may be planned and initiated, and for example, suitable control protocols with suitable measurement sequences as explained above may be selected and, if appropriate, modified.

The MR system 1 and the control device 13 may also include a plurality of other components that are not shown individually but are normally present in such systems (e.g., a network interface to link the whole system to a network, and to be able to exchange raw data and/or image data, as well as other data such as patient-related data or control protocols).

How suitable raw data may be acquired and MR images therefrom may be reconstructed through the irradiation of RF pulses and the generation of gradient fields is known to the person skilled in the art and will not be described in greater detail here. Similarly, a variety of measurement sequences, such as, for example, EPI measurement sequences or measurement sequences for generating diffusion-weighted images, are known to the person skilled in the art.

The methods and devices described above are merely exemplary embodiments, and the invention can be varied by a person skilled in the art without departing from the scope of the invention as defined by the claims. Therefore, the method and the breathing monitoring device 30 were primarily explained in conjunction with a contrast agent-supported recording of medical image data. The invention is, however, not restricted to an MR image recording combined with a contrast agent provided in advance. The invention may instead also essentially be applied to the recording of images without additional administration of contrast agents. For the sake of completeness, the use of the indefinite article "a" or "an" does not preclude the relevant feature from also being present plurally. Similarly, the expression "unit" does not preclude this consisting of a plurality of components that may also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance (MR) imaging method with an imaging workflow, the MR imaging method comprising:
   outputting at least one breath-holding command to a patient;
   acquiring MR imaging data with the MR imaging method that is usable with free breathing;
   detecting a breathing movement of the patient based on the MR imaging data acquired with the MR imaging method that is usable with free breathing;
   determining a time relationship between the breathing movement of the patient and the at least one breath-holding command, the determining of the time relationship comprising determining a time difference between a time instant of the outputting of the at least one breath-holding command to the patient and a time instant of the detected breathing movement; and
   modifying the imaging workflow as a function of the determined time relationship wherein modifying the imaging workflow comprises deciding whether and how the time instant of the outputting of the at least one breath-holding command is to be temporally adjusted, whether and how a start time instant of the MR imaging is to be temporally adjusted, or a combination thereof.

2. The MR imaging method of claim 1, wherein determining the time relationship comprises determining the time relationship as to whether the patient has realized the at least one breath-holding command; and
   wherein modifying the imaging workflow comprises deciding whether the at least one breath-holding command is to be entirely omitted.

3. The MR imaging method of claim 1, wherein determining the time relationship comprises determining with which time difference the at least one breath holding command was performed by the patient.

4. The MR imaging method of claim 1, wherein detecting the breathing movement of the patient takes place based on raw data resulting from acquired MR signals.

5. The MR imaging method of claim 1, wherein the imaging workflow is a clocked workflow.

6. The MR imaging method of claim 1, wherein modifying the imaging workflow as the function of the determined time relationship comprises modifying the imaging workflow as a function of the determined time difference.

7. The MR imaging method of claim 1, wherein an imaging method with an iterative reconstruction technique is used as the MR imaging method.

8. The MR imaging method of claim 7, wherein the MR imaging method includes radial scanning.

9. The MR imaging method of claim 8, wherein the MR imaging method comprises an iGRASP imaging method.

10. A breathing monitoring device comprising:
a processor configured to:
output a breath-holding command to a patient to hold breath;
start acquisition of magnetic resonance (MR) imaging data with an MR imaging method that is usable with free breathing;
detect a breathing movement of the patient based on the MR imaging data acquired with the MR imaging method that is usable with free breathing;
determine a time relationship between the breathing movement of the patient and the breath-holding command, the determination of the time relationship comprising determination of a time difference between a time instant of the output of the breath-holding command to the patient and a time instant of the detected breathing movement; and
modify an imaging workflow as a function of the determined time relationship, the modification of the imaging workflow comprising a decision whether and how the time instant of the output of the breath-holding command is to be temporally adjusted, whether and how a start time instant of the MR imaging is to be temporally adjusted, or a combination thereof.

11. A magnetic resonance (MR) imaging system comprising:
a radio-frequency transmit system;
a gradient system;
a controller configured, in order to perform a desired measurement based on a predetermined pulse sequence, to actuate the radio-frequency transmit system and the gradient system; and
a breathing monitoring device comprising a processor, the processor being configured to:
output a breath-holding command to a patient to hold breath;
start acquisition of MR imaging data with an MR imaging method that is usable with free breathing;
detect a breathing movement of the patient based on the MR imaging data acquired with the MR imaging method that is usable with free breathing;
determine a time relationship between the breathing movement of the patient and the breath-holding command, the determination of the time relationship comprising determination of a time difference between a time instant of the output of the breath-holding command to the patient and a time instant of the detected breathing movement; and
modify an imaging workflow as a function of the determined time relationship, the modification of the imaging workflow comprising a decision whether and how the time instant of the output of the breath-holding command is to be temporally adjusted, whether and how a start time instant of the MR imaging is to be temporally adjusted, or a combination thereof.

12. A computer program product comprising a non-transitory computer-readable storage medium, the non-transitory computer-readable storage medium storing instructions executable by a computer of a magnetic resonance imaging system for a magnetic resonance (MR) imaging with an imaging workflow, the instructions comprising:
outputting at least one breath-holding command to a patient;
acquiring MR imaging data with an MR imaging method that is usable with free breathing;
detecting a breathing movement of the patient based on the MR imaging data acquired with the MR imaging method that is usable with free breathing;
determining a time relationship between the breathing movement of the patient and the at least one breath-holding command, the determining of the time relationship comprising determining a time difference between a time instant of the outputting of the at least one breath-holding command to the patient and a time instant of the detected breathing movement; and
modifying the imaging workflow as a function of the determined time relationship, wherein modifying the imaging workflow comprises deciding whether and how the time instant of the outputting of the at least one breath-holding command is to be temporally adjusted, whether and how a start time instant of the MR imaging is to be temporally adjusted, or a combination thereof.

13. In a non-transitory computer-readable storage medium that stores instructions executable by a computer of a magnetic resonance imaging system for a magnetic resonance (MR) imaging with an imaging workflow, the instructions comprising:
outputting at least one breath-holding command to a patient;
acquiring MR imaging data with an MR imaging method that is usable with free breathing;
detecting a breathing movement of the patient based on the MR imaging data acquired with the MR imaging method that is usable with free breathing;
determining a time relationship between the breathing movement of the patient and the at least one breath-holding command, the determining of the time relationship comprising determining a time difference between a time instant of the outputting of the at least one breath-holding command to the patient and a time instant of the detected breathing movement; and
modifying the imaging workflow as a function of the determined time relationship wherein modifying the imaging workflow comprises deciding whether and how the time instant of the outputting of the at least one breath-holding command is to be temporally adjusted, whether and how a start time instant of the MR imaging is to be temporally adjusted, or a combination thereof.

14. The non-transitory computer-readable storage medium of claim 13, wherein determining the time relationship comprises determining the time relationship as to whether the patient has realized the at least one breath-holding command; and wherein modifying the imaging workflow comprises deciding whether the at least one breath-holding command is to be entirely omitted.

15. The non-transitory computer-readable storage medium of claim 13, wherein determining the time relationship comprises determining with which time difference the at least one breath holding command was performed by the patient.

* * * * *